United States Patent [19]

Mosley et al.

[11] Patent Number: 5,752,945
[45] Date of Patent: May 19, 1998

[54] ABSORBENT ARTICLE WITH LIQUID TRANSFER LAYER

[75] Inventors: Ellen Mosley, Ventnor; Raymond K. Whitby, Ocean City, both of N.J.; Vera Owen, Maumelle, Ark.

[73] Assignee: FiberTech Group, Inc., Landisville, N.J.

[21] Appl. No.: 846,003

[22] Filed: Apr. 25, 1997

[51] Int. Cl.[6] .................................................. A61F 13/15
[52] U.S. Cl. ........................................ 604/370; 604/378
[58] Field of Search ............................... 604/358, 370, 604/378, 379, 385.1

[56] References Cited

U.S. PATENT DOCUMENTS

| | | | |
|---|---|---|---|
| 4,223,677 | 9/1980 | Anderson | 604/378 X |
| 5,437,653 | 8/1995 | Gilman et al. | 604/378 |
| 5,505,719 | 4/1996 | Cohen et al. | 604/378 X |
| 5,525,407 | 6/1996 | Yang | 604/378 X |
| 5,643,240 | 7/1997 | Jackson et al. | 604/378 |
| 5,649,916 | 7/1997 | Dipalma et al. | 604/378 |

*Primary Examiner*—Mary Beth Jones
*Attorney, Agent, or Firm*—Juettner Pyle Piontek & Underwood

[57] ABSTRACT

An absorbent article such as a disposable diaper or sanitary article has an absorbing core and an outer porous cover sheet to allow transfer of liquids through the cover sheet and into the core. A liquid transfer sheet in the form of a nonwoven fabric is located between the cover sheet and the core. The transfer sheet has at least two layers, with the layer facing the cover sheet having relatively coarse fibers, and the layer facing the core having relative fine fibers. The arrangement allows more efficient transfer of liquids to the core while minimizing wetback.

10 Claims, 1 Drawing Sheet

ABSORBENT ARTICLE WITH LIQUID TRANSFER LAYER

BACKGROUND OF THE INVENTION

This invention relates to articles for absorbing liquids, such as diapers, or other sanitary articles, in which an outer porous layer of fabric is disposed over an absorbent core, and a liquid handling layer of fabric is disposed between the outer layer and the absorbent core.

Modern disposable absorbent articles such as diapers and other sanitary articles generally comprise an absorbent core made from cellulose pulp or other organic fibers and/or a superabsorbing polymer in powder or fiber form. The portion of the core which faces the body is covered with a soft nonwoven fabric or perforated film. In addition, it is common to provide an additional layer of nonwoven fabric between the outer fabric layer and the core. The purpose of this layer, often referred as a liquid transport or surge layer, is to accommodate a surge of liquid and to allow more time for the core to absorb the liquid without overflow and leaking. A second function of the intermediate layer is to isolate the core from the cover layer fabric or top sheet and to minimize rewetting of the cover layer.

Many proposals have been made with regard to liquid transfer layers. Generally, the use of bulky fabrics having a high void volume and high wet compression resistance have been proposed, with the high void volume providing transient liquid handling capacity, and the compression resistance improving rewet values. Many of these proposals may be considered as deficient, inasmuch as a surge of liquid is allowed to pass through and concentrate on one area of the core, thereby reducing efficiency of absorption. Also, these fabrics tend to increase the overall bulkiness of the article.

It is also known to incorporate a body facing layer in an absorbent article in which two layers are bonded to each other. The outer layer is generally a soft layer of fine fibers, and the inner layer has a large pore size and serves as a traditional liquid transport layer.

SUMMARY OF THE INVENTION

In accordance with the present invention, an absorbent article is provided with an inner absorbent core and an outer porous layer, together with a liquid transport layer between the core and outer layer. The liquid transport layer is characterized as having at least two distinct layers bonded together. The layer which faces the outer cover layer comprises fibers which are coarser than the layer which faces the core. The coarse layer provides wet and dry resilience and liquid holding capacity. The fine layer works in conjunction with the coarse layer to provide lateral wicking or flow paths, in order to more uniformly distribute the liquid across the core, thereby enhancing absorption rate. The two layers also operate in conjunction to provide a one way valve effect toward the core and improved rewet properties. Improvements are realized, for example, in comparison with single layer and more bulky transfer layers. The outer or cover layer also protects the relatively harsh surface of the coarse transfer layer.

In accordance with a preferred embodiment, the nonwoven fabric in the liquid transport layer is a two layered fabric, with the layers being bonded together, such as by thermal bonding. The coarse layer comprises fibers having a denier in the order of from about 5 to about 15 dpf, and the fine layer comprises fibers having a denier of from about 1.2 to about 3 dpf, with an average denier difference between the two layers being at least about 3 dpf. The basis weight of the fabric in each layer is from about 7 to about 50 grams per square meter (gsm), and the caliper or thickness of the overall fabric in from about 40 to about 90 mils at a load of 0.01 psi. The fabric layers should also be wettable and have a good wet compression resistance.

The absorbent article of the present invention can be furnished with the transfer layer being relatively thin in comparison to prior art structures. The two layer transfer web provides superior liquid handling characteristics compared to a single layer made from different denier fibers, and also compared to a two layer web which is arranged with the finer fibers facing the cover web.

DESCRIPTION OF THE PREFERRED EMBODIMENTS

Figure 1:
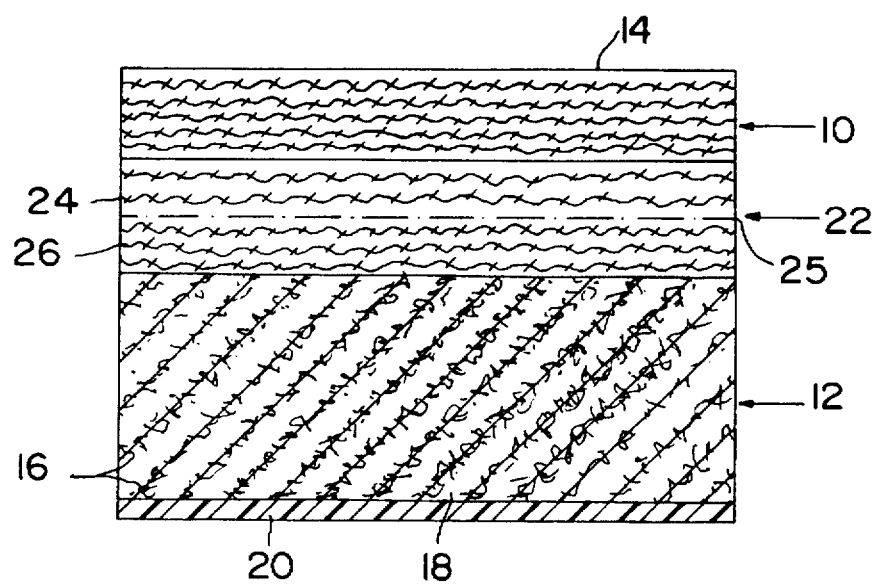
FIG. 1 is an enlarged schematic cross sectional fragmentary view of the absorbent article of the present invention.

As shown in FIG. 1, the absorbent article of the present invention comprises an outer nonwoven soft porous fabric layer 10 and an inner absorbing core 12. Outer layer 10 is a nonwoven fabric of polymer fibers bonded together to provide a porous, planar web. The fabric, for example, can be made from relatively fine (less than 3.0 dpf) polyolefin fibers or bicomponents fibers which are thermally point bonded together, such as by calendering between engraved calender rolls, or through-air bonding with hot air, or by other processes, well known in the art of nonwovens. Since the fabric will be in contact with the body, the outwardly facing surface 14 should have a soft feel or surface, and the fabric should be porous to allow rapid transfer of liquids. In some situations, it may be possible to substitute an apertured film for the layer 10, or an apertured film which is covered by fibers which are either adhesively or thermally bonded to the film. In the case of conventional point bonded nonwoven fabrics made from polyolefin, especially polypropylene, the basis weight of the fabric will be in the order of from about 15 to about 30 gsm.

The core 12 is a relatively thick and highly absorbent structure designed to permanently absorb and retain repeated insults of liquids. Cores, such as used in disposable diapers, are well known in the art and typically comprise unbonded cellulose pulp fibers, with a quantity of superabsorbent polymer (SAP) 16 disposed therein in particle or fiber form. Other variants include cores without SAP particles, as well as cores in which the SAP is the primary or only absorption media. The core 12 is typically provided in a flat rectangular or hourglass shape, depending on the size, fit and other practical parameters of the disposable garment or other article.

In many cases, the surface 18 of the core 12 remote from the outer porous fabric 10 is provided with a layer 20 of a liquid impermeable material, such as a impermeable, or semi-permeable (breathable) film. The outer layer of the film 20 is sometimes covered with a layer of fibers or is otherwise treated to simulate a cloth-like fabric.

The foregoing descriptions of the cover layer 10, absorbent layer 12 and outer layer 20 are intended as general descriptions of conventional components used in present day disposable sanitary or absorbent articles and garments, and many variants are known and are described in the prior art. In many cases, the core 12 will be substantially thicker than that shown in FIG. 1, and the thickness of the fabric and film layers has been exaggerated for sake of clarity.

In accordance with the present invention, a liquid transfer layer 22 of a particular configuration is disposed between the cover layer 10 and the core 12 and in surfacewise contact with the cover and core. The transfer layer 22 comprises are least two separate and distinct layers 24 and 26 bonded together at the interface 25 between the layers. The fibers of the fabric in the outwardly facing layer 24 adjacent to the cover layer 10 are coarser than the fibers in the layer 26 adjacent to the core 12.

For the coarse layer 24, a majority of the fibers of the fabric have a denier of from about 5 to about 15 dpf. For the fine layer 26, the majority of the fibers of the fabric have a denier of from about 1.2 to about 3 dpf. The average difference in denier of the fibers in the two layers is at least 3 dpf and most preferably at least 5 dpf. The basis weight of each layer can vary widely and is in the order of about 7 to about 50 gsm, depending upon application. The thickness of the composite fabric is from about 40 to about 90 mils at 0.01 psi load. The thickness can be greater than 90 mils.

Various types of fibers may be used to make the layered fabric. Preferably, such fibers are polymer fibers having heat fusible surfaces to enable thermal bonding by conventional methods. Particularly suitable fibers comprise crimped bicomponent fibers in which the fibers have an outer heat fusible surface in a sheath-core or side-by-side configuration. such as polyester/polyethylene and polypropylene/polyethylene. Other suitable fibers include those made from homopolymers such as polyethylene. polypropylene and polyester, as well as mixtures of fibers. The fibers are preferably hydrophilic or wettable, and if necessary, can be topically treated with small amounts of a surface acting agent such as a surfactant.

The layered fabric 22 can be prepared by forming a web of unconsolidated fibers of a first average denier on a moving conveyor, forming a second web of fibers of a second average denier over or on the first web, and then simultaneously bonding the fibers in each layer and the two layers together. For example, the first fiber web may be deposited from a first carding machine, and the second fiber web may be deposited from a second card in line with the first. The superimposed webs are then bonded together with the application of heat. A preferred method of bonding is through-air bonding in which the web is supported, and hot air or steam is forced through the web, causing the fiber surfaces to soften and weld together without applying any significant pressure. Other potentially suitable methods include pattern bonding or point bonding using heat and possibly some degree of pressure, such as by calendering using an engraved roll.

As a non-equivalent alternative, it is possible to form one or both of the webs by a spunbond process in which continuous filaments of the polymer are spun or extruded, drawn and deposited on a conveyor, either a single or as multi-component filaments.

Regardless of the methods used to form the webs, webs should comprise fibers which are compatible in the sense that the layers are capable of thermally self-bonding to each other. Also, preferably the fibers in the transfer layer are hydrophilic or treated with a surface acting agent so that the fabric is more wettable than the cover fabric.

The present invention also contemplates a multiple layer liquid transfer fabric having three or more layers bonded together, with the outermost layer having coarser fibers than the innermost layer, as described herein.

As a specific example of a two layer liquid transfer layer, the fabric has a basis weight of 40 gsm. The coarse layer is a 20 gsm 10 denier polyester/polyethylene or polypropylene/polyethylene bicomponent fiber, and the inner layer is the same fiber having a denier of 3. when assembled as shown in FIG. 1, the transfer layer 22 will have an average pore size which is larger than the pore size of the cover layer 10.

Performance tests have been conducted to compare the layered structure of the present invention with other structures. In one case, the other structure was a single layer fabric of the same basis weight having a uniform blend of the different denier fibers. In the other case, the fabric was made in the same two layers, but the layer facing the top sheet was composed of the finer fibers. In both cases the liquid handling properties of the arrangement was superior to the other fabrics, especially in providing lower rewet values.

In terms of other properties, the layered fabric 22 will have a compression resiliency in excess of 80 percent. A specific example is a two layer fabric having a basis weight of 40 gsm in which the coarse layer is a 20 gsm 10 denier polypropylene/polyethylene bicomponent fiber, and the other layer is the same fiber having a denier of 3. When assembled as shown in FIG. 1, the transfer layer will have an average pore size which is larger than the pore size of the cover layer 10.

Initial performance tests have been made to compare the two layer acquisition layer of the present invention to a single blended layer material of the same basis weight using the same type, denier and type of fiber. The transfer layer of the present invention generally provides good liquid handling capacity and allows more efficient absorption of liquids into the core, while minimizing any tendency for liquid to be transferred back to the outer cover layer. The transfer layer is also less bulky than many prior art structures and is generally less than 2.5 mm.

What is claimed is:

1. An absorbent article for absorption of liquids. said article comprising an absorbent core, an outer porous nonwoven cover sheet over said core, and a nonwoven liquid transfer fabric comprising first and second separate layers of fibers bonded together, said first layer of said transfer fabric being adjacent said nonwoven cover sheet and comprising fibers of a first average denier and said second layer of said transfer fabric comprising fibers of a second average denier which is smaller than said first average denier, and wherein said porous cover sheet and said liquid transfer fabric have first and second average pore sizes, and wherein the average pore size of said cover sheet is smaller than the average pore size of said liquid transfer fabric.

2. The absorbent article of claim 1 wherein said fibers in said first and second layers differ by at least 3 dpf.

3. The absorbent article of claim 2 wherein the fibers in the first layer have an average denier of from about 5 to about 15 dpf, and the fibers in the second layer have an average denier of from about 1.2 to about 3 dpf.

4. The absorbent article of claim 1 wherein each of said first and second layers has a basis weight of from about 7 to about 50 gsm.

5. The absorbent article of claim 1 wherein said first and second layers comprise thermally bondable bicomponent fibers.

6. The absorbent article of claim 1 wherein said first and second layers comprise heat bondable thermoplastic fibers and said transfer fabric is bonded by through-air bonding.

7. The absorbent article of claim 1 wherein said first and second layers comprise thermally bondable bicomponent filaments.

8. The absorbent article of claim 1 wherein the deniers of the fibers in the first and second layers differ by more than 5 dpf.

9. The absorbent article of claim 1 wherein said nonwoven fabric comprises fibers having a denier of less than 3 dpf.

10. The absorbent article of claim 1 wherein said liquid transfer fabric has a thickness of from about 40 to about 90 mils.

* * * * *